United States Patent
Yoon et al.

(10) Patent No.: US 9,783,893 B2
(45) Date of Patent: Oct. 10, 2017

(54) METHOD OF MANUFACTURING MICRO-ARRAY SUBSTRATE

(71) Applicants: GACHON UNIVERSITY OF INDUSTRY—ACADEMIC COOPERATION FOUNDATION, Seongnam-Si, Gyeonggi-Do (KR); GIL MEDICAL CENTER, Incheon (KR)

(72) Inventors: Young Soo Yoon, Seoul (KR); Seung Hyun Jee, Seoul (KR); Seon Tae Kim, Seongnam-Si (KR)

(73) Assignees: GACHON UNIVERSITY OF INDUSTRY-ACADEMIC COOPERATION FOUNDATION (KR); GIL MEDICAL CENTER (KR)

( * ) Notice: Subject to any disclaimer, the term of this patent is extended or adjusted under 35 U.S.C. 154(b) by 0 days.

(21) Appl. No.: 14/902,541

(22) PCT Filed: Jul. 8, 2015

(86) PCT No.: PCT/KR2015/007054
§ 371 (c)(1),
(2) Date: Feb. 24, 2016

(87) PCT Pub. No.: WO2016/076506
PCT Pub. Date: May 19, 2016

(65) Prior Publication Data
US 2016/0298241 A1 Oct. 13, 2016

(30) Foreign Application Priority Data
Nov. 12, 2014 (KR) .................. 10-2014-0157051

(51) Int. Cl.
*C23C 16/455* (2006.01)
*C23C 16/02* (2006.01)
(Continued)

(52) U.S. Cl.
CPC ............... *C23C 26/00* (2013.01); *B01J 19/00* (2013.01); *B05B 7/26* (2013.01); *B05D 5/00* (2013.01);
(Continued)

(58) Field of Classification Search
CPC ................ C23C 16/0227; C23C 16/45525
See application file for complete search history.

(56) References Cited

U.S. PATENT DOCUMENTS

| | | | | |
|---|---|---|---|---|
| 4,580,505 A | * | 4/1986 | Golden | .................. B01J 8/1836 110/245 |
| 5,328,720 A | * | 7/1994 | Emken | .................. B01J 8/1827 118/303 |

(Continued)

FOREIGN PATENT DOCUMENTS

| | | |
|---|---|---|
| KR | 20040017904 A | 3/2004 |
| KR | 20100052631 A | 5/2010 |
| KR | 20120018688 A | 3/2012 |

OTHER PUBLICATIONS

Fici, Dolores A., et al., "A protein multiplex microarray substrate with high sensitivity and specificity". Journal of Immunological Methods 363 (2010) 60-66.*

(Continued)

*Primary Examiner* — Bret Chen
(74) *Attorney, Agent, or Firm* — Renaissance IP Law Group LLP (57) ABSTRACT

A method of manufacturing a microarray substrate having improved reliability and mass-production properties uses a vapor of a surface-reforming material, and includes washing a base substrate, supplying the vapor of the surface-reforming material into a container to which the base substrate is
(Continued)

provided, and coupling the vapor of the surface-reforming material to a surface of the base substrate to form a self-assembled monolayer.

8 Claims, 4 Drawing Sheets

(51) Int. Cl.

| | |
|---|---|
| C23C 26/00 | (2006.01) |
| G01N 33/53 | (2006.01) |
| B05B 7/26 | (2006.01) |
| B05D 5/00 | (2006.01) |
| B81C 1/00 | (2006.01) |
| B81C 99/00 | (2010.01) |
| C03C 17/28 | (2006.01) |
| C12N 15/10 | (2006.01) |
| C03C 17/30 | (2006.01) |
| B01J 19/00 | (2006.01) |
| C23C 14/12 | (2006.01) |
| B01L 3/00 | (2006.01) |

(52) U.S. Cl.
CPC ...... B81C 1/00007 (2013.01); B81C 99/0025 (2013.01); C03C 17/28 (2013.01); C03C 17/30 (2013.01); C12N 15/1093 (2013.01); C23C 14/12 (2013.01); G01N 33/53 (2013.01); B01L 3/502707 (2013.01); C03C 2217/20 (2013.01); C03C 2218/15 (2013.01); C03C 2218/31 (2013.01)

(56) References Cited

U.S. PATENT DOCUMENTS

| | | | | |
|---|---|---|---|---|
| 2002/0182603 | A1* | 12/2002 | Chapman, Jr. ... | G01N 33/54386 506/32 |
| 2003/0164179 | A1* | 9/2003 | Kamikawa ........ | H01L 21/67781 134/25.4 |
| 2004/0258927 | A1* | 12/2004 | Conzone ................ | B82Y 30/00 428/429 |
| 2005/0074898 | A1* | 4/2005 | Datwani ................ | B82Y 15/00 436/180 |
| 2007/0249060 | A1* | 10/2007 | Kirschner .............. | B82Y 15/00 436/173 |
| 2008/0311337 | A1 | 12/2008 | Veinot et al. | |
| 2012/0141676 | A1* | 6/2012 | Sershen ............ | C23C 16/45551 427/255.23 |
| 2014/0274771 | A1* | 9/2014 | Elizazu ............ | G01N 33/54353 506/9 |

OTHER PUBLICATIONS

Fixe, F., et al., "Thin film micro arrays with immobilized DNA for hybridization analysis". Mat. Res. Soc. Symp. Proc. vol. 723: Molecularly Imprinted Materials—Sensors and Other Devices. Symposia held in San Francisco, CA on Apr. 2-5, 2002, O2.3, pp. 125-130.*
Moorcroft, Matthew J., et al., "In situ oligonucleotide synthesis on poly(dimetylsiloxane): a flexible substrate for microarray fabrication". Nucleic Acids Research, 2005, vol. 33, No. 8 e75, pp. 1-10.*
International Search Report of PCT/KR2015/007054 mailed on Aug. 17, 2015.
Notification of Transmittal of Translation of the International Preliminary Report on Patentability including Written Opinion of PCT/KR2015/007054 dated May 26, 2017.

* cited by examiner

METHOD OF MANUFACTURING MICRO-ARRAY SUBSTRATE

TECHNICAL FIELD

The present invention relates to a method of manufacturing a microarray substrate and an apparatus for manufacturing a microarray substrate, and more particularly, to a method of manufacturing a microarray substrate to form a self-assembled monolayer having improved uniformity and reliability, and an apparatus for manufacturing a microarray substrate for the same.

BACKGROUND ART

Recently, in accordance with development of a genome project, genome nucleotide sequences of various organisms have been identified, thus increasing an interest in biomicrochips and microarrays of the chips. The microarray is extensively used in gene expression profiling, genotyping, detection of mutation and polymorphism such as SNP, protein and peptide analysis, screening of latent drugs, and development and manufacturing of new drugs.

In the microarray used in the aforementioned analysis or detection, a plurality of oligomer probes should be provided on a substrate, and the plurality of oligomer probes are fixed to the substrate to have different sequences for each region. In this case, a functional group layer mediating coupling of the oligomer probes, that is, a self-assembled monolayer (SAM), may be formed on the substrate to fix more stable and integrated oligomer probes. Subsequently, a step of attaching DNA or protein to the functional group layer is performed to manufacture and use the microarray. When the microarray substrate including the self-assembled monolayer that is the functional group layer is produced using the aforementioned method, there is a difficulty in that several process steps are performed, accordingly, there is a limitation in terms of reliability or mass-production properties of the microarray substrate.

Particularly, in a typical technology such as Korean Patent Application Laid-Open No. 10-2004-0017904, slide glass is dipped in a solution including a functional group layer material mediating coupling of oligomer probes dissolved in a solvent such as alcohol to form a functional group layer in order to manufacture a microarray substrate. The aforementioned dipping method has a limitation in that in order to form the functional group layer, a coupling reaction is performed on a surface of slide glass to reduce a concentration of the functional group layer material present in the solution. The concentration is not maintained according to a position of a container containing the solution and a time and thus it is very difficult to control the concentration of the functional group layer material in the solution, accordingly, it is not easy to uniformly form the functional group layer on the entire surface of slide glass using the dipping method. Accordingly, there is a limitation in that uniformity and reliability of the microarray substrate are significantly reduced.

(Patent Document 1) Korean Patent Application Laid-Open No. 10-2004-0017904

DISCLOSURE OF THE INVENTION

Technical Problem

The present invention has been made in an effort to solve the aforementioned limitations of the typical technology, and to provide a method and an apparatus for manufacturing a microarray substrate to form a self-assembled monolayer using a vapor of a surface-reforming material, thus improving uniformity and reliability.

Technical Solution

In order to accomplish the aforementioned technical object, a method of manufacturing a microarray substrate according to an embodiment of the present invention may include washing a base substrate, supplying a vapor of a surface-reforming material into a container to which the base substrate is provided, and coupling the vapor of the surface-reforming material to a surface of the base substrate to form a self-assembled monolayer.

The method may further include activating the surface of the base substrate to form a —OH group on the surface of the washed base substrate.

The method may further include supplying an inert gas into a bubbler receiving the surface-reforming material in a liquid phase to move the vapor of the material of the self-assembled monolayer by the inert gas, and the bubbler may be heated to a temperature between room temperature and a boiling point of the surface-reforming material.

The container may be filled with a mixture gas including the vapor of the surface-reforming material and an inert gas, internal pressure of the container may be maintained at 0.001 atm to 2 atm, or a liquid may be provided into the container to dip the base substrate in the liquid.

The surface-reforming material may be at least one functional group selected from —NH$_2$, —SH, epoxy, acrylic, cyanato, —COOH, —CHO, a thiol group, a silanol group, a phosphine group, L-lysine, amine, aldehyde, epoxy, and polylysine (ploy-L-lysine).

The base substrate may include at least one material selected from glass, metal, a polymer, silicone, and a compound semiconductor.

An apparatus for manufacturing a microarray substrate according to another embodiment of the present invention may include a container receiving a base substrate, a gas supply tube connected to a gas distributor provided at one side of the container, a bubbler connected to the gas supply tube and receiving a surface-reforming material in a liquid phase, a carrier gas supply unit supplying an inert gas into the surface-reforming material in the liquid phase, and a discharge portion provided at another side of the container. A self-assembled monolayer including the surface-reforming material may be formed on a surface of the base substrate using a vapor of the surface-reforming material supplied by the inert gas.

The gas distributor and the discharge portion may be disposed at both ends of the base substrate to face each other.

The gas distributor may include a plurality of holes, and an effective cross-sectional area of the plurality of holes per a unit area of a surface of the gas distributor may increase as it travels from a central region to an edge region in the gas distributor.

Advantageous Effects

According to the method of manufacturing the microarray or the apparatus for manufacturing the microarray according to the present invention, it is possible to form the self-assembled monolayer using the vapor of the surface-reforming material to constantly adjust the concentration of the surface-reforming material coupled to the surface of the base substrate while the concentration is not changed according to a time or a temperature, thus manufacturing the microarray substrate having improved reliability and mass-production properties.

Further, it is possible to adjust the temperature of the bubbler receiving the surface-reforming material solution and generating the vapor of the surface-reforming material and the flow rate of the inert gas provided to the bubbler, or a process condition such as the concentration of the surface-reforming material provided to the base substrate or internal pressure of the container, thus controlling properties of the self-assembled monolayer using a simple method.

In addition, when the apparatus for manufacturing the batch-type microarray substrate is used to laminate a plurality of base substrates in parallel and supply the vapor of the surface-reforming material and thus form the self-assembled monolayer, it is possible to mass produce the microarray substrates having uniform properties simultaneously.

MODE FOR CARRYING OUT THE INVENTION

Hereinafter, various embodiments according to the present invention will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the figures, the dimensions may be exaggerated for illustration of the embodiments, and like reference numerals refer to like elements throughout.

A microarray chip should have a plurality of oligomer probes, and the plurality of oligomer probes should have different sequences for each region and be fixed to a microarray substrate. A self-assembled monolayer (SAM) including a functional group mediating coupling of the oligomer probes needs to be formed and thus reform a surface of a base substrate 100 in order to fix the more stable and integrated oligomer probes to the microarray substrate.

Figure 1:
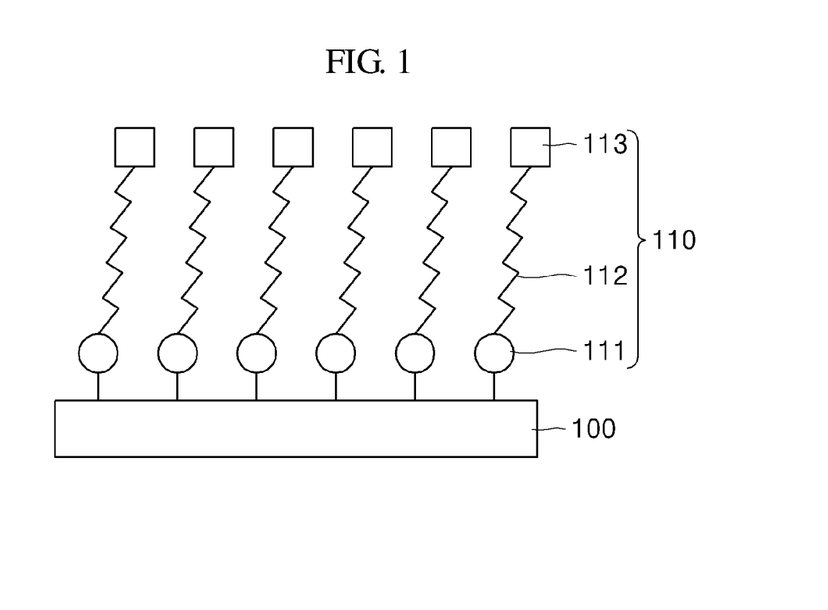
FIG. 1 is a conceptual view of a self-assembled monolayer structure manufactured according to an embodiment of the present invention.

FIG. 1 is a conceptual view of a self-assembled monolayer structure manufactured according to an embodiment of the present invention. A self-assembled monolayer 110 formed on the base substrate 100 includes a head group 111 coupled to a surface of the base substrate 100, a backbone 112 mostly including an alkyl chain, and an end group 113 including a functional group providing functionality.

The head group 111 may be selected according to a type of the base substrate 100, silanes may be selected in the case of frequently used slide glass or silicon, and thiols (—SH) may be selected in the case that the base substrate 100 is metal. In addition, the backbone 112 connecting the head group and the end group may be hydrocarbon chains or fluorocarbon chains. Lastly, the end group 113 may be selected from various functional groups according to a portion to be reacted afterward, that is, a type of materials to be attached.

Figure 2:
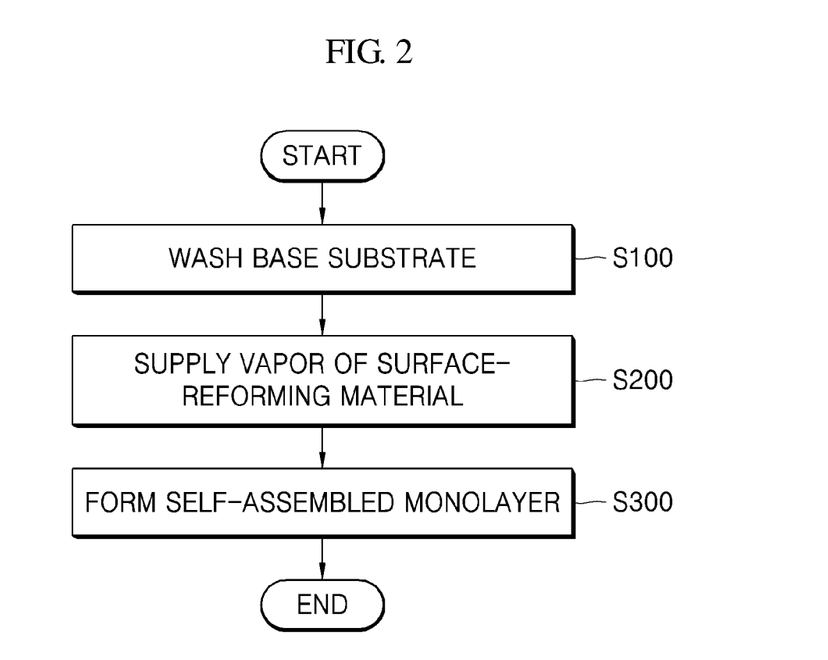
FIG. 2 is a flowchart of a method of manufacturing a microarray according to an embodiment of the present invention.
Figure 3:
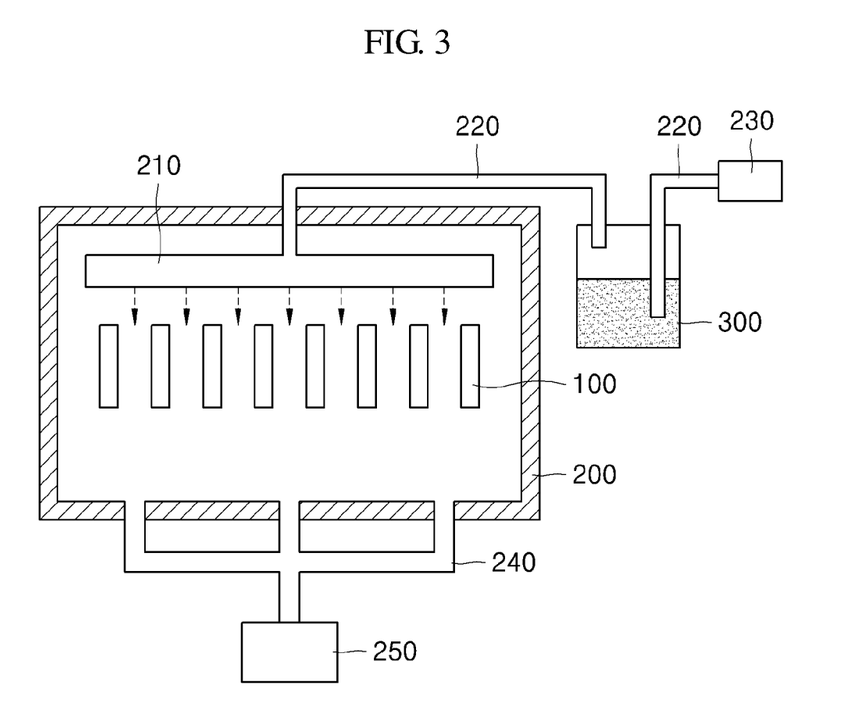
FIG. 3 is a schematic view of an apparatus for manufacturing a microarray according to an embodiment of the present invention.
Figure 4:
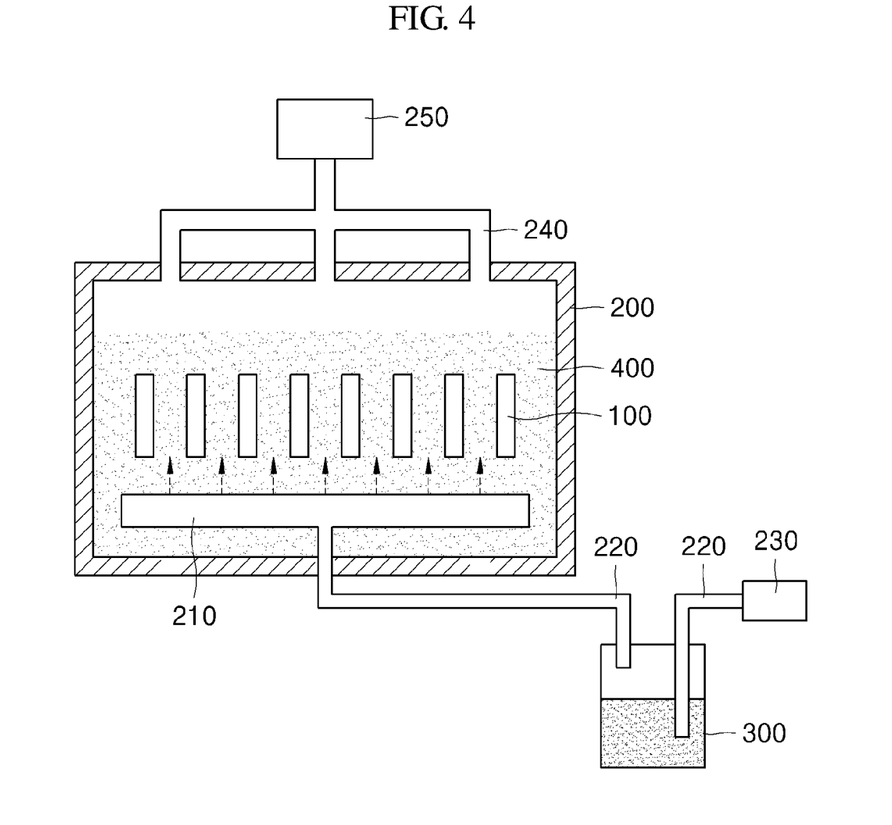
FIG. 4 is a schematic view of an apparatus for manufacturing a microarray according to another embodiment of the present invention.

FIG. 2 is a flowchart of a method of manufacturing a microarray according to an embodiment of the present invention, and FIGS. 3 and 4 are schematic views of apparatuses for manufacturing a microarray according to an embodiment of the present invention.

Referring to FIGS. 2 to 4, a method of manufacturing a microarray substrate according to an embodiment of the present invention may include washing a base substrate in operation S100, supplying a vapor of a surface-reforming material into a container to which the base substrate is provided in operation S200, and coupling the vapor of the surface-reforming material to a surface of the base substrate to form a self-assembled monolayer in operation S300.

The base substrate 100 is the most basic constitution forming the microarray substrate, and acts to support the self-assembled monolayer as will be described below and constitute a basic structure of the microarray substrate. The base substrate 100 may include at least one material selected from glass, metal, a polymer, silicone, and a compound semiconductor. The base substrate 100 may be washed through various methods so that foreign substances are not present on the surface before the base substrate 100 is provided into a container 200 used to manufacture the microarray substrate.

Subsequently, the washed base substrate 100 is introduced into the container 200, and the vapor of the surface-reforming material is then supplied into the container 200. The surface-reforming material may be a material constituting the end group 113 of the self-assembled monolayer 110 and including at least one functional group selected from —NH$_2$, —SH, epoxy, acrylic, cyanato, —COOH, —CHO, a thiol group, a silanol group, a phosphine group, L-lysine, amine, aldehyde, epoxy, and polylysine (ploy-L-lysine). For example, in the case that the base substrate 100 is glass, silanes may be selected as the head group 111 coupled to the surface of the base substrate 100, accordingly, the surface-reforming material may be 3-aminopropyltriethoxysilane and the like as a silane-based material including at least one functional group selected from —NH$_2$, —SH, epoxy, acrylic, cyanato, —COOH, —CHO, a thiol group, a silanol group, a phosphine group, L-lysine, amine, aldehyde, epoxy, and polylysine (ploy-L-lysine).

Meanwhile, the method may further include supplying an inert gas as a carrier gas into a bubbler 300 receiving the surface-reforming material in the liquid phase to perform bubbling and thus move the vapor of the surface-reforming material by the inert gas in order to introduce the vapor of the surface-reforming material present in the liquid phase at a predetermined temperature such as room temperature at a constant concentration that is not changed according to a time into the container 200. The bubbler 300 may be heated to a temperature between room temperature and a boiling point of the surface-reforming material to adjust vapor pressure of the surface-reforming material present over the surface-reforming material received in the bubbler 300. The surface-reforming material in the liquid phase has predetermined vapor pressure even at room temperature, but the temperature of the bubbler 300 is adjusted to stably supply the vapor of the surface-reforming material at a constant concentration to the container 200. When the bubbler is heated to the boiling point of the surface-reforming material or more, it is difficult to control the concentration of the surface-reforming material supplied by being moved by the carrier gas due to very high vapor pressure, and thus the temperature may be maintained at the boiling point or lower. The bubbler 300 may be heated from room temperature by a temperature corresponding to 30% to 80% of a difference in temperature of room temperature and the boiling point in order to stably supply the vapor of the surface-reforming material in a controllable range. The bubbler 300 may be maintained at room temperature to 200° C.

As described above, a flow rate of the inert gas supplied from an inert gas supply unit 230 connected to the bubbler 300 through a gas supply tube 220 or vapor pressure of the surface-reforming material in the bubbler 300 (or the temperature of the bubbler) may be adjusted to allow a vapor amount of the surface-reforming material moved by the inert gas to be supplied into the container 200 to be constant and adjust the vapor amount of the surface-reforming material, if necessary.

Subsequently, the vapor of the surface-reforming material provided into the container reaches the surface of the base substrate 100 to be coupled to the surface of the base substrate 100, thus forming the self-assembled monolayer. In the case that the silane-based material including at least one functional group selected from —$NH_2$, —SH, epoxy, acrylic, cyanato, —COOH, —CHO, a thiol group, a silanol group, a phosphine group, L-lysine, amine, aldehyde, epoxy, and polylysine (ploy-L-lysine) is used as the surface-reforming material, silicone included in the silane-based material is coupled to the surface of the base substrate 100 to form the self-assembled monolayer. Unlike a typical technology of dipping the base substrate in a solution including the surface-reforming material dissolved in a solvent such as alcohol to form the self-assembled monolayer, in the case of a vaporization method according to the present invention, the surface-reforming material in a vapor phase may be directly provided at a constant concentration or in a constant supply amount to the base substrate 100 to form the self-assembled monolayer 110 having uniform properties regardless of a time or a position.

Meanwhile, the method of manufacturing the microarray according to the present invention may further include activating the surface of the base substrate to form a —OH group on the surface of the washed base substrate so that the vapor of the surface-reforming material is coupled well to the surface of the base substrate 100. Hydrogen peroxide, ammonia water, and deionized water (DI water) are mixed at a ratio of 1:1:5, and the washed base substrate 100 may be then dipped for 5 minutes to 20 minutes to induce a base (OH) on the surface of the base substrate, thus introducing preferable formation of the self-assembled monolayer as will be described below.

A dry method or a wet method may be performed to form the self-assembled monolayer using the vapor of the surface-reforming material in the method of manufacturing the microarray according to the present invention.

In the case of the dry method, the container 200 may be filled with a mixture gas including the vapor of the surface-reforming material and the inert gas (see FIG. 3), and internal pressure of the container 200 may be maintained at 0.001 atm to 2 atm. The concentration (or material amount) of the surface-reforming material present in the container 200 may be controlled using internal pressure of the container 200 together with the temperature of the bubbler 300 and the flow rate of the inert gas.

In the case of the wet method, while the container 200 is filled with a liquid such as water to dip the base substrate 100 in a liquid 400, the vapor of the surface-reforming material is supplied from a lower end of the container 200 (see FIG. 4). In the case of the wet method, the container 200 may not be entirely filled with the liquid, a portion of an upper end of the container may be filled with the mixture gas, and the mixture gas may be maintained under pressure of 0.001 atm to 2 atm.

Meanwhile, in the case that the concentration of the surface-reforming material in the liquid is changed according to a time, since the amount of the surface-reforming material supplied to the surface of the base substrate 100 is not constant, a material not dissolving the surface-reforming material may be selected as the liquid 400. However, even in the case that the surface-reforming material is dissolved in the liquid 400, since a time during which the vapor of the surface-reforming material is supplied to the lower end of the container 200, passes through the base substrate 100, and is discharged to the outside of the container (that is, retention in the container) is short, the amount of the surface-reforming material dissolved in the liquid 400 is very small, and thus the concentration of the surface-reforming material may not be changed according to a time or process progress.

The self-assembled monolayer is formed using a dipping method of dipping the base substrate 100 in the solution including the dissolved surface-reforming material to couple the surface-reforming material to the base substrate in order to manufacture the typical microarray substrate. Accordingly, there are limitations in that the concentration of the surface-reforming material present in the solution is reduced and it is difficult to control the concentration of the material of a functional group layer in the solution according to a position of the container containing the solution and a time. However, the surface-reforming material may be supplied to the surface of the base substrate and the microarray substrate having improved reliability and mass-production properties may be manufactured regardless of a process progress state, a time, and a position using the vapor of the surface-reforming material having the constant concentration provided into the container by the inert gas which is the carrier gas in the method of manufacturing the microarray according to the present invention.

Further, the temperature (the vapor pressure) of the bubbler receiving the surface-reforming material solution and generating the vapor of the surface-reforming material and the flow rate of the inert gas provided to the bubbler may be adjusted, or a process condition such as an internal pressure of the container may be adjusted to control properties of the self-assembled monolayer using a simple method.

Meanwhile, in the case that the dipping method of the typical technology is performed, a post-washing step of removing the solvent is positively necessary after the dipping method is performed, but the post-washing is not necessary in the dry method of the present invention. Naturally, if necessary, the treated substrate may be washed to remove foreign substances and/or unreacted surface-reforming materials from the surface of the microarray substrate even in the method of manufacturing the microarray substrate according to the present invention.

Referring to FIGS. 3 and 4, an apparatus for manufacturing a microarray substrate according to the present invention may include a container 200 receiving a base substrate 100, a gas supply tube 220 connected to a gas distributor 210 provided at one side of the container 200, a bubbler 300 connected to the gas supply tube 220 and receiving a surface-reforming material in a liquid phase, a carrier gas supply unit 230 supplying an inert gas into the surface-reforming material in the liquid phase, and a discharge portion 240 provided at another side of the container 200. A self-assembled monolayer 110 including the surface-reforming material may be formed on a surface of the base substrate 100 using a vapor of the surface-reforming material supplied by the inert gas.

Although not shown in FIGS. 3 and 4, a flowmeter and a valve may be further provided to the gas supply tube 220 and the discharge portion 240 in order to control the concentration of the vapor of the surface-reforming material supplied into the container 200.

The base substrate 100 provided into the container 200 may be a batch-type apparatus for manufacturing a microarray to form the self-assembled monolayer while a plurality of base substrates are disposed in parallel, if necessary. Even in the case of the batch type, the concentration of the vapor of the surface-reforming material in the container may be constant in terms of a time and a space to mass produce the microarray substrate having improved reliability. Further, when a process variable such as internal pressure of the container 200 is adjusted to maintain the concentration of the vapor of the surface-reforming material staying in the container, a plurality of stages including the base substrates 100 arranged in parallel may be laminated to surface-treat more base substrates in the batch-type apparatus for manufacturing the microarray.

The gas distributor 220 through which the mixture gas of the vapor of the surface-reforming material and the inert gas is uniformly introduced into the container, and the discharge portion 240 connected to an external pump or a discharge duct 250 to discharge the vapor of the unreacted surface-reforming material to the outside may be disposed at both ends of the base substrate 100 to face each other, thus constantly supplying the vapor of the surface-reforming material to the surface of the base substrate 100.

Figure 5:
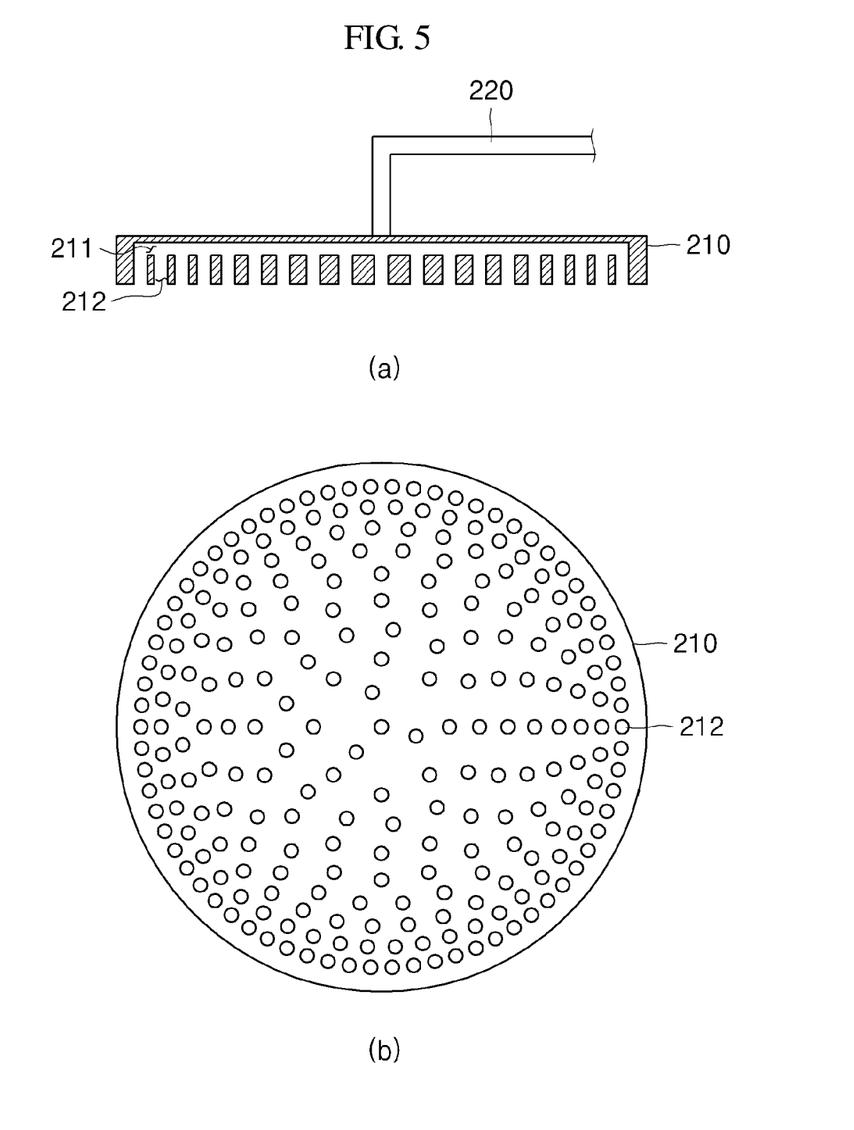
FIG. 5 is a cross-sectional view of a gas distributor according to an embodiment of the present invention.

FIG. 5 is a cross-sectional view of the gas distributor according to an embodiment of the present invention.

The gas distributor 210 includes an internal space 211 connected to the gas supply tube 220 at an intermediate portion thereof, and a plurality of holes 212 communicating with the internal space 211 to supply the vapor of the surface-reforming material into the container 200. Since a central region of the gas distributor 210 is adjacent to the gas supply tube 220, the vapor of the surface-reforming material supplied through the gas supply tube 220 may be more easily discharged through the central region of the gas distributor 210, accordingly, amounts of the vapors of the surface-reforming materials supplied from the central and edge regions of the gas distributor 210 may be different according to a position. Therefore, an effective cross-sectional area of a plurality of holes 212 per a unit area of the surface of the gas distributor 210 may be constituted to increase as it travels from the central region to the edge region in the gas distributor, thus constantly supplying the vapor of the surface-reforming material into the container 200 regardless of the position of the gas distributor 210. In FIG. 5, an interval between the holes 212 is wider in the central region than in the edge region, but the intervals between the holes may be the same while the size of the hole may be smaller in the central region than in the edge region. A method of changing the effective cross-sectional area of a plurality of holes 212 per the unit area of the surface of the gas distributor 210 according to the position is not particularly limited.

According to the method of manufacturing the microarray or the apparatus for manufacturing the microarray according to the present invention, the self-assembled monolayer may be formed using the vapor of the surface-reforming material to constantly adjust the concentration of the surface-reforming material coupled to the surface of the base substrate according to a time or a temperature, thus manufacturing the microarray substrate having improved reliability and mass-production properties.

Further, the temperature of the bubbler receiving the surface-reforming material solution and generating the vapor of the surface-reforming material and the flow rate of the inert gas provided to the bubbler may be adjusted, or a process condition such as the concentration of the surface-reforming material provided to the base substrate or internal pressure of the container may be adjusted to control properties of the self-assembled monolayer using a simple method.

In addition, when the batch-type apparatus for manufacturing the microarray substrate is used to laminate a plurality of base substrates in parallel and supply the vapor of the surface-reforming material and thus form the self-assembled monolayer, it is possible to mass produce the microarray substrates having uniform properties simultaneously.

Although the preferable embodiments of the present invention have been illustrated and described, the present invention is not limited to the aforementioned embodiments. Therefore, it will be readily understood by those skilled in the art that various modifications and equivalents can be made thereto without departing from the gist of the present invention defined by the appended claims. Accordingly, the technical scope of the present invention is to be determined by the following claims.

What is claimed is:

1. A method of manufacturing a microarray substrate, comprising:
   washing a plurality of base substrates;
   supplying a vapor of a surface-reforming material into a container to which the plurality of base substrates are provided, wherein the plurality of base substrates are arranged in parallel with each other in batch type inside the container, and wherein supplying the vapor of the surface-reforming material includes supplying the vapor of the surface-reforming material into the container from a gas distributor provided at a first side of the container, wherein the gas distributor includes a plurality of holes, and wherein an effective cross-sectional area per a unit area of a surface of the gas distributor increases from a central region to an edge region in the gas distributor;
   coupling the vapor of the surface-reforming material to a surface of the plurality of base substrates to form a self-assembled monolayer; and
   discharging the vapor of the surface-reforming material through a discharge portion provided at a second side of the container, wherein the plurality of base substrates are positioned between the first and second sides of the container.

2. The method of claim 1, further comprising:
   activating the surface of each of the plurality of base substrates to form a —OH group on the surface of the washed base substrate.

3. The method of claim 1, further comprising:
   supplying an inert gas into a bubbler receiving the surface-reforming material in a liquid phase to move the vapor of the surface-reforming material by the inert gas.

4. The method of claim 3, wherein the bubbler is heated to a temperature between room temperature and a boiling point of the surface-reforming material.

5. The method of claim 1, wherein the container is filled with a mixture gas including the vapor of the surface-reforming material and an inert gas, and internal pressure of the container is maintained at 0.001 atm to 2 atm.

6. The method of claim 1, wherein a liquid is provided into the container to dip the plurality of base substrates in the liquid.

7. The method of claim 1, wherein the surface-reforming material includes at least one functional group selected from the group consisting of: —$NH_2$, —SH, epoxy, acrylic, cyanato, —COOH, —CHO, a thiol group, a silanol group, a phosphine group, L-lysine, amine, aldehyde, epoxy, and polylysine (ploy-L-lysine).

8. The method of claim 1, wherein each of the plurality of base substrates includes at least one material selected from the group consisting of: glass, metal, a polymer, silicone, and a compound semiconductor.

* * * * *